United States Patent [19]

Schiff et al.

[11] 4,345,847

[45] Aug. 24, 1982

[54] AUTOMATIC BRAKE SEQUENCING FOR OVERHEAD SUPPORT ARM ASSEMBLIES

[75] Inventors: Charles M. Schiff, Aurora; Eric K. Maxon, Englewood; Ronald E. West, Littleton, all of Colo.

[73] Assignee: Technicare Corporation, Solon, Ohio

[21] Appl. No.: 105,360

[22] Filed: Dec. 19, 1979

[51] Int. Cl.³ .............................................. F16C 11/00
[52] U.S. Cl. .................................... 403/103; 248/124; 73/621
[58] Field of Search .................... 403/84, 91, 103, 62, 403/64; 248/124, 282, 283; 73/621

[56] References Cited

U.S. PATENT DOCUMENTS

| | | | |
|---|---|---|---|
| 3,348,799 | 10/1967 | Junkel et al. | 248/283 |
| 3,637,233 | 1/1972 | Hoppl et al. | 248/124 X |
| 4,014,207 | 3/1977 | Meyer et al. | 73/621 |
| 4,244,227 | 1/1981 | Rudolph et al. | 73/621 |

*Primary Examiner*—Andrew V. Kundrat
*Attorney, Agent, or Firm*—Audley A. Ciamporcero, Jr.

[57] ABSTRACT

A roller-switch and cam, located at an intermediary joint of a plural arm overhead assembly, delays the unlocking of a brake at a next adjacent joint until the joint at which the cam and switch are located has diverged a predetermined angle from alignment.

6 Claims, 6 Drawing Figures

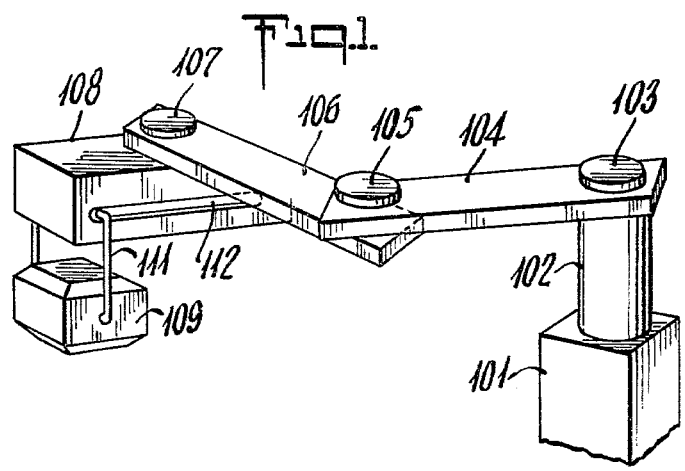
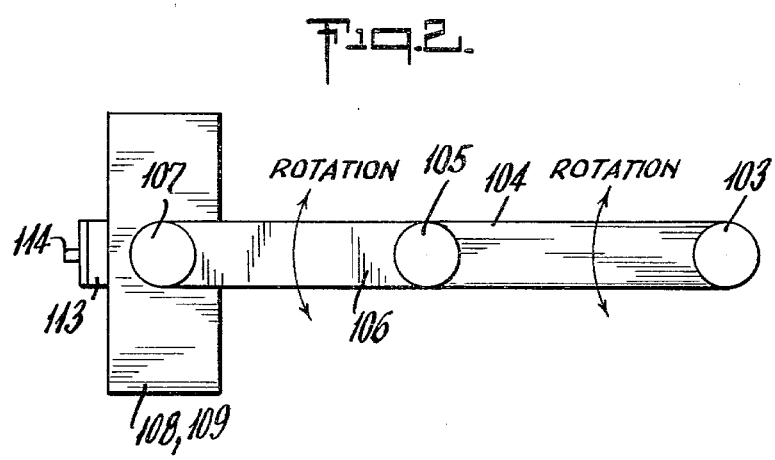
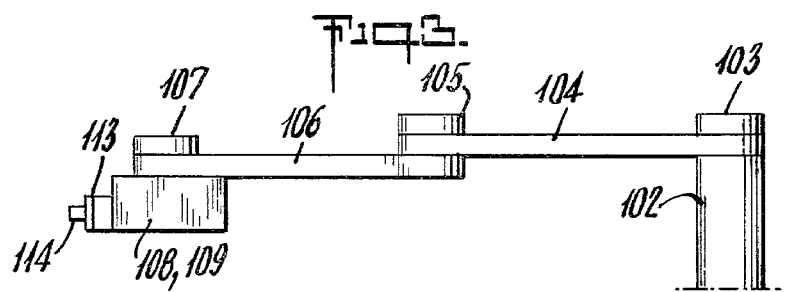

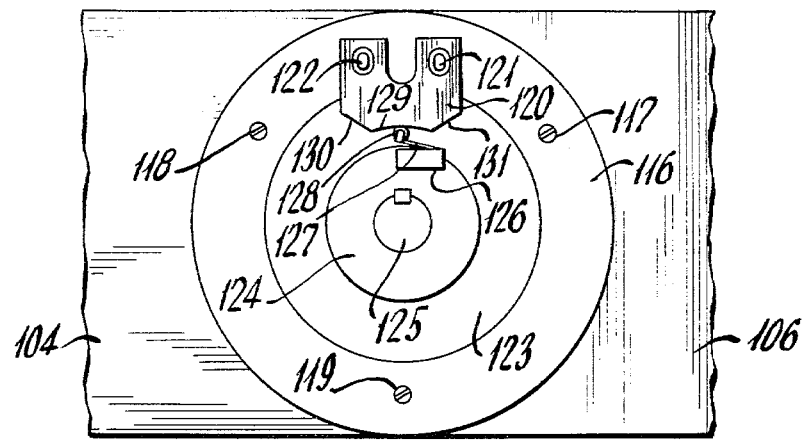
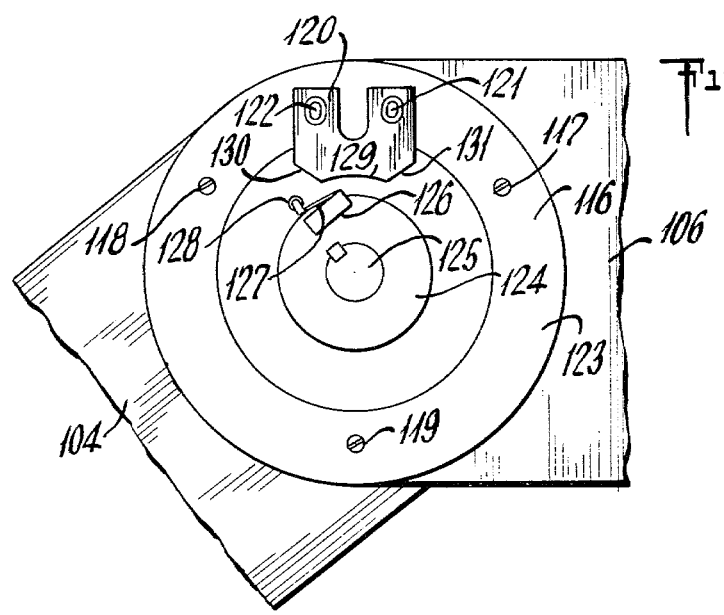
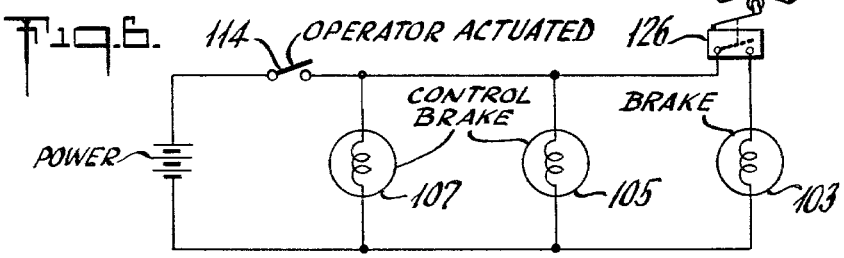

AUTOMATIC BRAKE SEQUENCING FOR OVERHEAD SUPPORT ARM ASSEMBLIES

FIELD OF THE INVENTION

This invention relates to apparatus having segmented, jointed arm assemblies, and more particularly to electromechanical control of brake means located at the joints of such segments.

BACKGROUND OF THE INVENTION

Many types of medical equipment employ a diagnostic device, such as an ultrasound scanning head, which needs to be freely movable in all directions within a given space in order to apply it to select portions of a reclining or otherwise stationary patient. A preferred approach is to utilize a segmented arm assembly, depending outwardly from a fixed, vertically adjustable standard. Typically, the arm assembly is above the patient, and includes three or so arm segments separated by horizontal pivot joints, with each segment being rotatable in the horizontal plane.

Such systems obviously afford great flexibility to the operator, in terms of positioning the diagnostic head in contact with the patient, and for the most part they allow the operator a rather complete and precise control. There exists a problem, however, in such segmented assemblies when the respective segments are in alignment or approximately in alignment. During such times, the operator often has difficulty, when manipulating the arrangement from the outside perimeter of the assembly, in insuring that the several joints fold or rotate in the right sequence, and in the right direction. Chiefly, this is because the operator lacks a point of leverage with respect to the respective segments.

It is a principal object of the present invention to provide automatic sequencing controls whereby the operator who utilizes a multiple segment overhead arm assembly has requisite control over each individual segment, in terms of both direction and extent of rotation, whereby a diagnostic head may be properly and controllably applied to the patient.

SUMMARY OF THE INVENTION

In accordance with the principles of the present invention, each of the horizontal rotational joints of a multiple segment overhead arm assembly has a locking brake thereat, but not all are directly under the operator control. Instead, at least one of the brakes, and typically a centrally located one intermediate two of the rotatable arms, has located thereat a control/monitoring apparatus which separately regulates the locked or unlocked condition of a next adjacent joint, typically of the joint which is located at the stationary member. It is a function of this monitoring/control means to maintain such next adjacent joint in a locked condition until the arm segments with which the control means is associated, exceed a predetermined angle from a condition of alignment, whereupon the brake at such next adjacent joint is unlocked.

In a preferred embodiment, an overhead arm assembly includes a stationary vertical member, and a three segment horizontally rotatable arm assembly extending outwardly therefrom, with the three segments being sequentially interconnected with one another and with the stationary member by three pivot joints, each of which has a segment locking brake associated therewith. At the outer extremity, the operator has a brake lock/unlock control switch, which directly releases or locks the two outermost joints. Thereupon, the two outermost arms are freely rotatable under the operator control. A cam and switch combination at the center joint monitors the angular position of the two segments connected thereat, and when those segments exceed a predetermined angle relative to one another (i.e. a predetermined diversion from alignment), the cam actuates its associated switch to unlock the brake at the innermost joint. Thereupon, the operator may freely manipulate all three segments of the assembly, and directly lock or unlock all three brakes simultaneously to establish the desired configuration of the overhead arm assembly.

DESCRIPTION OF THE DRAWINGS

FIG. 1 shows an isometric view of an overhead arm assembly of the type to which the principles of the present invention relate;

FIGS. 2 and 3 show stylized top and side views of an assembly of the type shown in FIG. 1;

FIGS. 4 and 5 show a joint, brake, and cam actuated switch assembly in accordance with the principles of the present invention; and FIG. 6 shows a schematic diagram of a control circuit embodying the principles of the present invention.

BEST MODE FOR CARRYING OUT THE INVENTION

Referring first to FIG. 1, there is shown a more or less conventional overhead arm assembly of the type used in some ultrasound diagnostic imaging systems. In the figure, a fixed base 101 carries a vertical adjustment column 102, which in turn bears the overhead arm assembly. A first arm 104 rotates horizontally about a pivot and brake joint 103. A second arm 106 is connected to the outer extremity of arm 104, and rotates horizontally about a pivot and brake joint 105. A third segment 108 is connected to the outer extremity of arm 106, and rotates horizontally about a third pivot and brake joint 107. A diagnostic device, such as an ultrasound scanning head, depends from arm 108 by brackets 111, which in turn slide in track 112, thereby to provide yet another degree of freedom.

FIGS. 2 and 3 show respective top and side stylized views of the apparatus of FIG. 1, and illustrate the operation thereof. As will be noted, arm 104 rotates horizontally about pivot/brake 103, arm 106 rotates about pivot/brake 105, and arm 108 and device segment 109 move similarly with respect to pivot/brake 107. In FIGS. 2 and 3, arms 104 and 106 are shown to be in a condition of alignment. In conventional prior art fashion, switch means 114 and a handle 113 are provided for the operator to engage or release the brakes at 103, 105, and 107. It will be appreciated that, in the prior art, if all three brakes 103, 105 and 107 are simultaneously released, while the segments 104 and 106 are aligned as shown the operator has little control over the direction of rotation of the respective arms, chiefly because there is no single point of leverage between handle 113 and the point of rotation 103 about fixed column 102.

In accordance with the principles of the present invention, depression of brake unlocking switch 114 at handle 113 by the operator unlocks the brakes at pivot points 105 and 107, but so long as arm 104 is in line with, or nearly in line with arm 106, the brake located at pivot 103 automatically remains locked. Thereupon, when arm 106 pivots beyond a predetermined angle from the alignment or near alignment condition, the operator has sufficient leverage upon both arms 104 and 106, and therefore the brake at pivot point 103 is released.

The mechanism whereby this automatic locking and unlocking control may be maintained is preferably accomplished at pivot/brake location 105, and more particularly, a preferred configuration for such an arrangement is shown in FIGS. 4 and 5. In those figures, arms 104 and 106 are shown foreshortened for convenience. A brake body 116 is secured to the extremity of arm 106 by screws or bolts at 117, 118, and 119. Brake body 116 defines an opening through its center whereby a central shaft 125 attached to, and turning with arm 104, protrudes upwardly. A brake disc assembly 123 and 124 is connected to the shaft 125, whereby upon closure of the brake by operator actuation of switch 114, disc 123 is forced into contact with the brake body 116, and arms 104 and 106 are thereby locked into position. Such brake operation is conventional, and preferably is accomplished by electromagnetic actuation means.

A cam 120 is fastened to the brake body at points 121 and 122, and a switch 126 is attached to the disc brake base 124. The switch 126 has an outwardly directed spring arm 127, and at the extremity thereof, a roller 128 engages the cam 120. As will be noted, the cam 120 has a central surface 129 and outer surfaces 130 and 131 upon which the roller 128 rides. The surfaces 129, 130, and 131 are selected such that the spring arm 127 is deflected to open switch 126 so long as the roller 128 is riding upon central surface 129 of the cam 120; when spring arm 128 extends outwardly by virtue of roller 128 either riding on surfaces 130 or 131, or being unfettered as shown in FIG. 5, switch 126 is closed. In a preferred embodiment, the central surface 129 is on the circumference of a circle having a center of rotation at the center of the shaft 125. Hence surface 129 is concentric with the centers of rotation of the arms 104 and 106 at joint 105. The side surfaces 130 and 131 of cam 120 are further outward from the center of shaft 125 than is surface 129, and surfaces 130 and 131 are gradual, rather than stepwise or abrupt as they diverge from the surface 129. Hence, smooth engagement of the roller 128 with the cam 120 is promoted.

In a preferred embodiment, the arm 104 is to remain locked at pivot 103 until arm 106 is diverted approximately 10 to 15 degrees from alignment with arm 104. For such preferred embodiment, the surface 129 of cam 120 occupies a similar angle in each direction from the norm shown in FIG. 4. For example, should it be desired to unlock the brake at 103, thereby freeing arm 104, when arm 106 achieves a 15 degree angle in either direction from a condition of alignment, surface 129 is configured to fill an angle of 30 degrees, with the roller 128 being directly in the center of such surface (as shown in FIG. 4) when arms 104 and 106 are in alignment with one another.

FIG. 6 shows an illustrative schematic circuit operable in conjunction with the apparatus of FIGS. 1 through 5. As shown in FIG. 6, the respective brake controls 103, 105, and 107 are connected in parallel with one another, each being shown simply as a magnetic symbol, it being understood that the actuation of the brake may be achieved in conventional fashion through magnetically actuated apparatus, or alternative schemes. In any event, actuation of switch 114 by the operator couples power to brake controls 105 and 107, thereby unlocking those brakes and freeing elements 106 and 108 for operation. The delivery of power to the control of brake 103 is further restricted, however, based upon the conjunctive operation of cam 120 and switch 126. As noted previously with respect to FIGS. 4 and 5, power is not delivered to unlock brake 103 when the roller 128 is on the central surface 129 of cam 120. At other times, when switch 126 is closed, all three brakes 103, 105, and 107 are subject to the operator control by means of switch 114, and under such conditions, when switch 114 is open, all three brakes 103, 105, and 107 automatically lock.

It is to be understood that the foregoing sets forth illustrative and preferred embodiments of the principles of the present invention, but that numerous alternatives will occur to those of ordinary skill in the art without departure from the spirit or scope of the principles of the present invention. For example, in the broadest sense relating to the monitoring of angles, it will be apparent that, in replacement for the switch and cam approach taken in FIGS. 4 and 5, those of ordinary skill in the art may wish to employ magnetic reed switches, Hall effect switches, optical switching arrangements or the like, to monitor rotation of respective arms relative to the next adjacent arm, and for the actuation of the brake locking/unlocking mechanism upon the achievement of prescribed angles. Likewise, it will be apparent that many alternative cam configurations are suitable in substitution for the switch and cam arrangement scheme such as disclosed herein. For one instance, more complex cam surfaces may be employed in the form of mechanical logic to engender on/off/on/off or the like sequences, by providing corresponding successive increases and decreases in the radius of rotation of associated surfaces of the cam. Finally, it will be apparent that the angle monitoring scheme is not limited only to application at the particular joints set forth in the embodiment of FIGS. 1 through 3, but that various control schemes may be employed whereby separate monitoring functions as achieved at several or all of the joints (and regardless of how many segments are entailed in the overhead arm assembly), with "triggering" angles being selectively established and controlling at each respective joint.

What is claimed is:

1. In a system having an overhead arm assembly including at least three segments pivotably connected in sequence to one another and to a fixed member at three respective joints, apparatus for controlling locking and unlocking of said joints comprising:
    (a) first brake means at a first joint between first and second ones of said segments;
    (b) second brake means at a second one of said joints;
    (c) operator actuated first control means for selectively releasing said first brake means to permit said second segment to pivot relative to said first segment;
    (d) second control means, for detecting the angular orientation of said first and second segments relative to one another, and for responsively controlling said second brake means for unlocking said second brake means when said first and second segments achieve at least a predetermined angular divergence from a condition of alignment.

2. Apparatus as described in claim 1 wherein said second joint pivotably connects said first segment to said fixed member.

3. Apparatus as described in claim 1 wherein said second control means comprises cam means connected to said first segment at said first joint, and switch means connected to said second segment at said first joint, the operation of said switch means being established by its engagement with said cam.

4. Apparatus as described in claim 1 wherein said surface of said cam means engaging said switch means includes a first surface located along the circumference of a circle about said first joint, and two surfaces adjacent respective extremities of said first surface but being further spaced from said joint.

5. Apparatus as described in claim 4 wherein said switch means engages a central point of said first surface when said first and second segments are in said alignment position, and wherein said first surface extends through an angle equal to twice said predetermined angular divergence.

6. In a system having an overhead arm assembly including at least three segments pivotably connected in sequence to one another and to a fixed member at three respective joints, apparatus for controlling locking and unlocking of said joints comprising:
 (a) first brake means at a first joint between first and second ones of said segments;
 (b) second brake means at a second one of said joints, said second brake means being automatically locked when said first and second segments are in a given position of alignment with respect to each other;
 (c) operator actuated first control means for selectively releasing said first brake means to permit pivotable arrangement of said first segment relative to said second segment;
 (d) second control means, responsive to the orientation of said first and second segments relative to one another, for maintaining said second brake means in a locked condition for so long as said first and second segments are within a given angle of direct alignment with one another.

* * * * *